United States Patent [19]

Koppe et al.

[11] 4,031,244

[45] June 21, 1977

[54] PHARMACEUTICAL COMPOSITIONS CONTAINING A 1-(2,6-DIMETHYL-PHENOXY)-2-AMINO-ALKANE AND METHOD OF USE

[75] Inventors: Herbert Köppe; Karl Zeile; Werner Kummer; Helmut Stähle; Peter Danneberg, all of Ingelheim am Rhein, Germany

[73] Assignee: Boehringer Ingelheim GmbH, Ingelheim am Rhein, Germany

[22] Filed: Jan. 29, 1976

[21] Appl. No.: 653,296

Related U.S. Application Data

[60] Division of Ser. No. 511,063, Oct. 1, 1974, Pat. No. 3,954,872, which is a continuation-in-part of Ser. No. 86,983, Nov. 4, 1970, abandoned, which is a continuation-in-part of Ser. No. 871,619, Nov. 14, 1969, abandoned, which is a continuation of Ser. No. 667,665, Sept. 14, 1967, abandoned.

[30] Foreign Application Priority Data

Sept. 16, 1966 Germany .............................. 88950
Aug. 17, 1967 Germany .............................. 94024

[52] U.S. Cl. .............................................. 424/330
[51] Int. Cl.² ..................................... A61K 31/135
[58] Field of Search ...................................... 424/330

[56] References Cited

UNITED STATES PATENTS 3,235,597  2/1966  Mills et al. ..................... 260/570.7

OTHER PUBLICATIONS

Durant et al., *Journal Of Mecical Chemistry*, vol. 9, No. 1, pp. 22–27, (1966).

*Primary Examiner*—Albert T. Meyers
*Assistant Examiner*—Daren M. Stephens
*Attorney, Agent, or Firm*—Hammond & Littell

[57] ABSTRACT

Pharmaceutical compositions containing as an active ingredient a compound of the formula

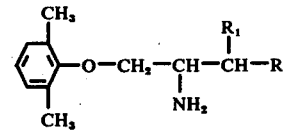

wherein R is hydrogen or alkyl of 1 to 3 carbon atoms, and $R_1$ is hydrogen or methyl, or a non-toxic, pharmacologically acceptable acid addition salt thereof; and a method of using the same as anticonvulsives and antiarrhythmics.

8 Claims, No Drawings

PHARMACEUTICAL COMPOSITIONS CONTAINING A 1-(2,6-DIMETHYL-PHENOXY)-2-AMINO-ALKANE AND METHOD OF USE

This is a division of copending application Ser. No. 511,063 filed Oct. 1, 1974, now U.S. Pat. No. 3,954,872 granted May 4, 1976; which in turn is a continuation-in-part of application Ser. No. 86,983, filed Nov. 4, 1970, now abandoned; which in turn is a continuation-in-part of application Ser. No. 871,619, filed Nov. 14, 1969, now abandoned; which in turn is a continuation of application Ser. No. 667,665, filed Sept. 14, 1967, now abandoned.

This invention relates to novel pharmaceutical compositions containing a 1-(2',6'-dimethyl-phenoxy)-2-aminoalkane, as well as to a method of using the same as anticonvulsives and antiarrhythmics.

More particularly, the present invention relates to pharmaceutical dosage unit compositions containing as an active ingredient a racemic mixture or optically active antipode of a 1-(2',6'-dimethyl-phenoxy)-2-amino-alkane of the formula

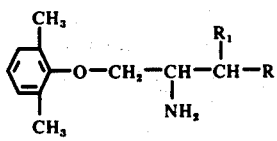

wherein R is hydrogen or alkyl of 1 to 3 carbon atoms, and $R_1$ is hydrogen or methyl, or a non-toxic, pharmacologically acceptable acid addition salt thereof.

The compounds embraced by formula I may be prepared by a number of methods involving well-known chemical principles, among which the following have proved to be particularly convenient and efficient:

Method A

By splitting off one or two monovalent or one bivalent protective group from a compound of the formula

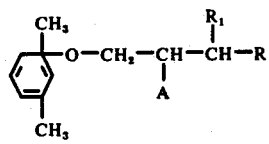

wherein R and $R_1$ have the same meanings as in formula I, and A is a secondary or tertiary amine group having one or two readily removable protective substituents, such as benzyl, phthalyl, toluenesulfonyl or formyl, attached thereto. The removal of the protective group may be achieved by conventional methods, such as by catalytic hydrogenation.

A starting compound of the formula II may be obtained by reacting a corresponding 1-(2',6'-dimethylphenoxy)-2-halo-alkane with a suitable primary or secondary amine, or by reacting a corresponding 1-(2',6'-dimethyl-phenoxy)-2-oxoalkane with a suitable primary amine under reducing conditions.

Method B

By reacting a compound of the formula

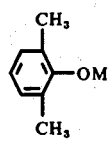

wherein M is hydrogen or a metal cation, with a compound of the formula

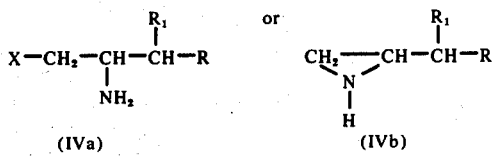

wherein R and $R_1$ have the same meanings as in formula I, and X is the radical of a reactive ester, such as halogen atom, particularly chlorine or bromine.

A compound of the formula IVa or IVb may be prepared by conventional methods, such as those described in British Pat. No. 765,849 or in Houben-Weyl, 4th Edition (1958), Vol. XI/2, pages 228–230.

Method C

By reducing a compound of the formula

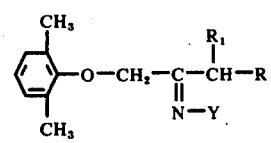

wherein R and $R_1$ have the same meanings as in formula I, and Y is hydrogen, hydroxyl or amino, with catalytically activated hydrogen or a complex metal hydride.

A starting compound of the formula V may be obtained by reacting a corresponding 1-(2',6'-dimethyl-phenoxy)-2-oxo-alkane with ammonia, hydroxylamine or hydrazine. A 1-(2',6'-dimethyl-phenoxy)-2-oxo-alkane, in turn, may be obtained by reacting a phenolate of the formula III with a 1-halo-2-oxo-alkane of corresponding carbon chain length.

The compounds of the formula I above contain an asymmetrically substituted carbon atom bonded to the free amino group and, occur in the form of racemic mixtures as well as optically active antipodes. The racemic mixtures may be divided into their optically active antipode components with conventional methods, for instance, by salt formation with optically active acids such as D-3-bromocamphor-8-sulfonic acid or dibenzoyl-D-tartaric acid. Another method of obtaining an optical antipode is by starting with the corresponding optically active antipode of compound II in method A.

The compounds of the formula I are organic bases and therefore form acid addition salts with inorganic or organic acids. Such acid addition salts may be obtained in customary fashion, such as by dissolving the free base in a suitable solvent and acidifying the solution with the desired inorganic or organic acid. Examples of non-toxic, pharmacologically acceptable acid addition salts are those formed with hydrochloric acid, hydrobromide acid, sulfuric acid, maleic acid, acetic acid, oxalic acid, lactic acid, tartaric acid, succinic acid, methanesulfonic acid, 8-chlorotheophylline or the like.

The following examples further illustrate the present invention and will enable others skilled in the art to understand it more completely. It should be understood, however, that the invention is not limited to the particular examples given below.

EXAMPLE 1

Preparation of 1-(2',6'-dimethyl-phenoxy)-2-amino-propane and its hydrochloride by method C 245 gm of 1-(2',6'-dimethyl-phenoxy)-propanone-(2)-oxime were dissolved in 1300 cc of methanol, and the solution was hydrogenated at 5 atmospheres gauge and 60° C. in the presence of Raney nickel. After the calculated amount of hydrogen had been absorbed, the catalyst was filtered off, the methanol was distilled out of the filtrate, and the residue raw 1-(2',6'-dimethyl-phenoxy)-2-amino-propane, was dissolved in ethanol. The resulting solution was acidified with ethereal hydrochloric acid, the acidic solution was allowed to cool, and the precipitate formed thereby was collected by vacuum filtration. The filter cake was dissolved in ethenol and recrystallized therefrom by addition of ether. 140.5 gm (51.4% of theory) of a substance having a melting point of 203°–205° C. were obtained, which was identified to be 1-(2', '-dimethyl-phenoxy)-2-amino-propane hydrochloride of the formula

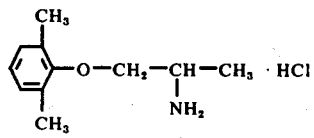

EXAMPLE 2

Preparation of 1-(2',6'-dimethyl-phenoxy)-2-amino-butane and its hydrochloride by method C 18.3 gm (0.095 mol) of 1-(2',6'-dimethyl-phenoxy)-butanone-(2) were refluxed with 14 gm (0.2 mol) of hydroxylamine hydrochloride in 100 cc of ethanol in the presence of 25 cc of water and 20 cc of pyridine, yielding 17.6 gm of raw 1-(2',6'-dimethyl-phenoxy)-butanone-(2)-oxime, which was dissolved in 50 cc of methanol, and the solution was hydrogenated at 60° C. and 5 atmospheres gauge in the presence of Raney nickel. After the calculated amount of hydrogen had been absorbed, the catalyst was filtered off, the methanol was distilled out of the filtrate, the residue digested with water, the aqueous mixture was acidified with hydrochloric acid, and the neutral component was extracted with ether. The acid aqueous phase was made alkaline with ammonia, the oily precipitate formed thereby was taken up in ether, the ethereal solution was dried over magnesium sulfate, and the ether was distilled off. The residue, 12.6 gm of 1-(2',6'-dimethyl-phenoxy)-2-amino-butane, was dissolved in ethanol, the resulting solution was acidified with ethereal hydrochloric acid, and the crystalline precipitate formed thereby was collected and recrystallized twice from ethanol/ether. 8.2 gm of a substance having a melting point of 210°–211° C. was obtained, which was identified to be 1-(2',6'-dimethyl-phenoxy)-2-amino-butane hydrochloride of the formula

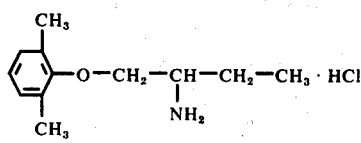

EXAMPLE 3

Using a procedure analogous to that described in Example 1, 1,(2',6'-dimethyl-phenoxy)-2-amino-pentane and its hychloride, m.p. 230°–231° C., were prepared from 1-(2',6'-dimethyl-phenoxy)-pentanone-(2).

EXAMPLE 4

Using a procedure analogous to that described in Example 2, 2-(2',6'-dimethyl-phenoxy)-2-amino-3-methylbutane and its hydrochloride, m.p. 170° C., were prepared from 1-(2',6'-dimethyl-phenoxy)-3-methyl-butanone-(2).

EXAMPLE 5

Preparation of 1-(2',6'-dimethyl-phenoxy)-2-amino-hexane and its hydrochloride by method C 13 gm (0.05 mol) of 1-(2',6'-dimethyl-phenoxy)-hexanone-(2)-oxime, obtained from 2',6'-dimetylphenoxymethyl-n-butyl ketone and hydroxylamine hydrochloride, were dissolved in methanol, and the solution was hydrogenated in a shaker autoclave at 60° C. and 5 atmospheres gauge in the presence of Raney nickel as a catalyst. After the theoretical amount of hydrogen had been absorbed, the catalyst was removed by vacuum filtration, and the methanol was distilled out of the filtrate. The residue was dissolved in ether, and the filtrate, an ethereal solution of the free base 1-(2',-6'-dimethyl-phenoxy)-2-amino-hexane, was acidified with ethereal hydrochloric acid to acid reaction of Congo Red. The white crystalline precipitate formed thereby was collected by vacuum filtration, and the filter cake was washed with ether and dried. 4.0 gm (31.1% of theory) of analytically pure and thin-layer chromatographically uniform 1-(2',6'-dimethyl-phenoxy)-2-amino-hexane hydrochloride, m.p. 209°–211° C., of the formula

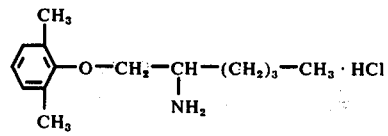

were obtained.

EXAMPLE 6

Preparation of 1-(2',6'-dimethyl-phenoxy)-2-amino-3-methylbutane and its hydrochloride by method C 10.3 gm (0.05 mol) of 1-(2',6'-dimethyl-phenoxy)-3-methyl-butanone-(2) were dissolved in a mixture of 75 cc of ethanol and 8.5 gm of ammonia, and the resulting solution was allowed to stand for 16 hours at 20° C. Thereafter, while stirring, a solution of 3.7 gm of sodium borohydride in 100 cc of ethanol was added dropwise at 20° C, the mixture was stirred for one hour more and was then acidified with hydrochloric acid. The acid solution was evaporated in vacuo, the residue was admixed with water, and the aqueous phase was made alkaline with sodium hydroxide, the precipitate formed thereby was extracted with ether, the ethereal solution was dried over magnesium sulfate, the ether was distilled off, the residue, the free base 1-(2',6'-dimethyl-phenoxy)-2-amino-3-methyl-butane, was taken up in methanol, and the resulting solution was acidified with ethereal hydrochloric acid. The precipitate formed thereby was collected and recrystallized from a mixture of methanol and ether, yielding .2 gm of 1-(2',6'-dimethyl-phenoxy)-2-amino-3-methyl-butane hydrochloride, m.p. 170° C, of the formula

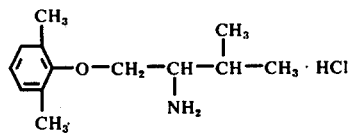

The compounds of the formula I, and their non-toxic, pharmacologically acceptable acid addition salts have useful pharmacodynamic properties. More particularly, they exhibit long-lasting anticonvulsive and anti-arrhythmic activities without significant concurrent sedative side effects in warmblooded animals, such as rats and mice. Examples of specific compounds which are especially effective as anticonvulsives are 1-(2,',6'-dimethyl-phenoxy)-2-amino-propane and its hydrochloride, and 1-(2',6'-dimethyl-phenoxy)-2-aminopentane and its hydrochloride.

The anticonvulsive activity of the compounds of the formula I and their non-toxic acid addition salts, as well as of certain isomers and homologs described in the prior art, was as certained by the electroshock method of Tooman et al, J. Neurophysiol. 9, 231 (1946), and their toxicities were determined by the standard method for determination of the median lethal dose ($LD_{50}$).

The following table shows illustrative and representative results obtained from these tests, where A = 1-(2',6'-xyloxyl)-2-amino-propane, described in Example I above;

B = N-methyl-2-(2',6'-xylyloxy)-ethylamine, disclosed by G. J. Durant et al, J. Med. Chem., Vol. 9, No. 1, 22 (1966);

C = 2-(2',6'-xylyloxy)-ethylamine, disclosed by G. J. Durant et al, supra; and

D = 3-(2',6'-xylyloxy)-propylamine, disclosed by Durant et al, supra.

| Compound | Anticonvulsive $ED_{50}$ mgm/kg mouse p.s. | $LD_{50}$ mgm/kg mouse p.o. | Therapeutic ratio $LD_{50}ED_{50}$ |
|---|---|---|---|
| Invention: | | | |
| A | 23 | 430 | 18.7 |
| Prior art: | | | |
| B | 80 | 216 | 2.7 |
| C | 115 | 740 | 6.4 |
| D | 216 | 580 | 2.7 |

For pharmaceutical purposes, the compounds of the formula I of their non-toxic acid addition salts are administered to warm-blooded animals perorally or parenterally as active ingredients in customary dosage unit compositions, that is, compositions in dosage unit form consisting essentially of an inert pharmaceutical carrier and one dosage unit of the active ingredient, such as tablets, coated pills, capsules, wafers, solutions, suspensions, emulsions, syrups, suppositories or the like. One dosage unit of the compounds of the formula I or their non-toxic acid addition salts for peroral administration is from 0.016 to 5 mgm/kg body weight, preferably 0.5 to 3.3 mgm/kg body weight; for parenteral administration, one dosage unit is from 0.0016 to 0.33 mgm/kg body weight.

A dosage unit composition pursuant to the instant invention may comprise one or more of the compounds of the formula I or a non-toxic acid addition salt thereof as an active ingredient, provided the total dosage unit range set forth above is not exceeded. In addition, such a dosage unit composition may comprise an effective dosage unit of one or more other pharmacodynamically active components, such as a tranquilizer of the benzodiazepine or phenothiazine type, or a spasmolytic of the scopolamine type.

The following examples illustrate a few dosage unit conpositions comprising a compound of the formula I or a non-toxic acid addition salt as an active ingredient, and represent the best modes contemplated of putting the invention to practical use. The parts by weight, unless otherwise specified.

EXAMPLE 7

Tablets

The tablet composition was compounded from the following ingredients:

| | | |
|---|---|---|
| 1-(2',6'-dimethyl-phenoxy)-2-amino-propane hydrochloride | 75.0 | parts |
| Lactose | 25.0 | " |
| Secondary calcium phosphate | 150.0 | " |
| Corn starch | 206.0 | " |
| Colloidal silicic acid | 12.0 | " |
| Stearic acid | 4.0 | " |
| Soluble starch | 8.0 | " |
| Total | 480.0 | parts |

Compounding procedure:

The phenoxypropane compound was intimately admixed with the lactose, the calcium phosphate, the corn starch and silicic acid, the resulting mixture was moistened with an aqueous solution of the soluble starch, and the moist mass was forced through a 1.5 mm-mesh screen. The moist granulate thus obtained was dried, admixed with the stearic acid, and the mixture was pressed into 480 mgm-tablets with the aid of a conventional tablet-making machine. Each tablet contained 75 mgm of the phenoxypropane compound and, when administered perorally to a warm-blooded animal about 60 kg body weight in need of such treatment, produced very good anticonvulsive and antiarrhythmic effects.

EXAMPLE 8

Coated pills

The pill core composition was compounded from the following ingredients:

| | | |
|---|---|---|
| 1-(2',6'-dimethyl-phenoxy)-2-amino-propane hydrochloride | 45 | parts |
| 1-(2',6'-methyl-phenoxy)-2-amino-pentane hydrochloride | 30 | " |
| Secondary calcium phosphate | 120 | " |
| Corn starch | 91 | " |
| Colloidal silicic acid | 7 | " |
| Magnesium stearate | 4 | " |
| Polyvinylpyrrolidone | 3 | " |
| Total | 300 | parts |

Compounding procedure:

The phenoxypropane compounds, the calcium phosphate, the corn starch and the silicic acid were intimately admixed with each other, the mixture was moistened with an aqueous solution of the polyvinylpyrrolidone, and the moist mass was forced through a 1.5 mm-mesh screen. The moist granulate thus obtained was dried, admixed with the magnesium stearate, and the mixture was pressed into 300 mgm-pill cores with the aid of a conventional tablet-making machine. The pill cores were subsequently coated with a thin shell of a coating composition consisting essentially of sugar, titaniumdioxide, talcum, gum arabic and polyvinylpyrrolidone. Each coated pill contained 45 mgm of the dimethylphenoxy-amino-propane compound and 30 mgm of the dimethylphenoxy-aminopentane compound and, when administered perorally to a warm-blooded animal of about 60 kg body weight in need of such treatment, produced very good antiarrhythmic and anticonvulsive effects.

EXAMPLE 9

Gelatin capsules

The capsule filler composition was compounded from the following ingredients:

| 1-(2',6'-dimethyl-phenoxy)-2-amino-propane maleate | 50 parts |
|---|---|
| Lactose | 150 " |
| Total | 200 parts |

Compounding procedure:

The phenoxypropane compound and the lactose were intimately admixed with each other, and 200 mgm-portions of the mixture were filled into individual gelatin capsules of suitable size. Each capsule contained 50 mgm of the phenoxypropane compound and, when administered perorally to a warm-blooded animal of about 60 kg body weight in need of such treatment, produced very good respiration-analeptic and anticonvulsive effects.

EXAMPLE 10

Tablets containing a compound of the formula I and a tranquilizer

The tablet composition was compounded from the following ingredients:

| 1-(2',6'-dimethyl-phenoxy)-2-amino-propane | 60 parts |
|---|---|
| 5-Phenyl-7-chloro-1,3-dihydro-3-hydroxy-2H-1,4-benzodiazepin-2-one | 30 " |
| Calcium phosphate | 150 " |
| Corn starch | 206 " |
| Colloidal silicic acid | 12 " |
| Magnesium stearate | 4 " |
| Soluble starch | 8 " |
| Total | 470 parts |

Compounding procedure:

The phenoxypropane compound, the benzodiazepinone compound, the calcium phosphate, the corn starch and the silicic acid were intimately admixed with each other, the mixture was moistened with an aqueous solution of the soluble starch, and the moist mass was forced through a 1.5 mm-mesh screen. The moist granulate thus obtained was dried, admixed with the magnesium stearate, and the mixture was pressed into 470 mgm-tablets with the aid of a conventional tablet-making machine. Each tablet contained 60 mgm of the phenoxypropane compound and 30 mgm of the benzodiazepinone compound and, when administered perorally to a warm-blooded animal of about 60 kg body weight in need of such treatment, produced very good anticonvulsive, antiarrhythmic and tranquilizing effects.

EXAMPLE 11

Hypodermic solution

The solution was compounded from the following ingredients:

| 1-(2',6'-dimethyl-phenoxy)-2-amino-propane hydrochloride | | 2.5 parts |
|---|---|---|
| Sodium salt of EDTA | | 0.2 " |
| Distilled water | q.s.ad | 1000.0 " by vol. |

Compounding procedure:

The phenoxypropane compound of the EDTA salt were dissolved in a sufficient amount of distilled water, the solution was filtered until free from suspended particles, the filtrate was filled into 2 cc-ampules, and the filled ampules were sterilized at 120° C for 20 minutes and then sealed. Each ampule contained 5 mgm of the phenoxypropane compound, and when the contents of one ampule were administered by intramuscular injection to a warm-blooded animal of about 60 kg body weight in need of such treatment, they produced very good anticonvulsive and antiarrhythmic effects.

It should be understood that any other compound embraced by formula I or a non-toxic acid addition salt thereof may be substituted for the particular phenoxyalkane compounds in Examples 7 through 11. Moreover, the amount of active ingredient in these examples may be varied to achieve the dosage unit ranges set forth in above and the amounts and nature of the inert pharmaceutical carrier components may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention of the scope of the appended claims.

We claim:

1. A pharmacodynamic dosage unit composition consisting essentially of an inert pharmaceutical carrier and an effective anticonvulsive or antiarrhythmic amount of a racemic or optically active compound of the formula

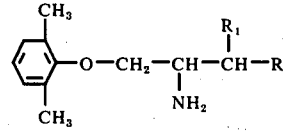

wherein R is hydrogen or alkyl of 1 to 3 carbon atoms and $R_1$ is hydrogen or methyl, or a non-toxic, pharmacologically acceptable acid addition salt thereof.

2. A composition of claim 1, where said compound is racemic or optically active 1-(2',6'-dimethyl-phenoxy)-2-amino-propane or a non-toxic, pharmacologically acceptable acid addition salt thereof.

3. A composition of claim 1, where said compound is racemic or optically active 1-(2',6'-dimethyl-phenoxy)-2-amino-pentane or a non-toxic, pharmacologically acceptable acid addition salt thereof.

4. A composition of claim 1, where said compound is racemic or optically active 1-(2',6'-dimethyl-phenoxy)-2-amino-hexane or a non-toxic, pharmacologically acceptable acid addition salt thereof.

5. The method of suppressing convulsions and alleviating cardiac arrhythmia in a warm-blooded animal in need of such treatment, which comprises administering to said animal an effective anticonvulsive or antiarrhythmic dose of a racemic or optically active compound of the formula

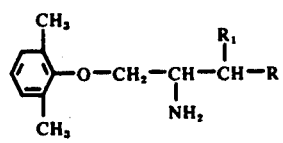

wherein R is hydrogen or alkyl of 1 to 3 carbon atoms and $R_1$ is hydrogen or methyl, or a non-toxic, pharmacologically acceptable acid addition salt thereof.

6. The method of claim 5, where said compound is racemic or optionally active 1-(2',6'-dimethyl-phenoxy)-2-amino-propane or a non-toxic, pharmacologically acceptable acid addition salt thereof.

7. The method of claim 5, where said compound is racemic or optically active 1-(2',6'-dimethyl-phenoxy)-2-amino-pentane or a non-toxic, pharmacologically acceptable acid addition salt thereof.

8. The method of claim 5, where said compound is racemic or optically active 1-(2',6'-dimethyl-phenoxy)-2-amino-hexane or a non-toxic, pharmacologically acceptable acid addition salt thereof.

* * * * *

UNITED STATES PATENT OFFICE
CERTIFICATE OF CORRECTION

Patent No. 4,031,244    Dated June 21, 1977

Inventor(s) HERBERT KOPPE; KARL ZEILE; WERNER DUMMER; HELMUT STAHLE; PETER DANNEBERG It is certified that error appears in the above-identified patent and that said Letters Patent are hereby corrected as shown below:

Col. 2, line 42   "and, occur" should read -- and, therefore, occur --

Col. 3, line 19   " (51.4%)" should read   -- (51.5%) --

Col. 3, line 20   " 1-(2',  '- " should read --   1-(2',6'- --

Col. 4, line 11   " 2, 2-(2'6'- " should read --   2, 1-(2',6'-

Col. 5, line 4    " .2gm " should read   -- 6.2 gm --

Col. 5, line 28   " as certained" should read -- ascertained --

Signed and Sealed this

Fourth Day of October 1977

[SEAL]

Attest:

RUTH C. MASON
Attesting Officer

LUTRELLE F. PARKER
Acting Commissioner of Patents and Trademarks